United States Patent
Broussard et al.

(10) Patent No.: US 6,444,848 B1
(45) Date of Patent: Sep. 3, 2002

(54) PROCESS FOR THE PREPARATION OF SYMMETRICAL DIACYLHYDRAZINES

(75) Inventors: Fabio Broussard, Brusaporto; Carlo Neri, San Donato Milanese; Flavio Somenzi, Cinisello Balsamo, all of (IT)

(73) Assignee: Great Lakes Chemical (Europe) GmbH (DE)

( * ) Notice: Subject to any disclaimer, the term of this patent is extended or adjusted under 35 U.S.C. 154(b) by 0 days.

(21) Appl. No.: 09/786,789

(22) PCT Filed: Dec. 3, 1999

(86) PCT No.: PCT/EP99/09760

§ 371 (c)(1),
(2), (4) Date: Mar. 9, 2001

(87) PCT Pub. No.: WO00/34227

PCT Pub. Date: Jun. 15, 2000

(30) Foreign Application Priority Data

Dec. 4, 1998 (IT) .......................... MI98A2631

(51) Int. Cl.[7] .............................................. C07C 241/00
(52) U.S. Cl. ........................ 564/148; 564/149; 564/311
(58) Field of Search ................................ 564/311, 148, 564/149

(56) References Cited

PUBLICATIONS

Bulow et al, Reports of the German Chemistry Society, vol. 41, 1908, pp. 1945–1947.*
Musante, Gazzeta Chimica Italiana, vol. 48, 1954, pp. 209–229.*
Musante, Gazzeta Chimica Italiana, vol. 84, 1954, pp209–229.*
The Aldrich Catalog, Handbook of Fine Chemicals, 1996–97.*

Transformazioni ad opera del calore di alcuni cinconcinil–idrazido di beta–chetoesteri e sintesi nel gruppo del pirazol–pirone, Carlo Musante, Gazzetta Chimica Italiana (Roma), vol. 84, Nov. 5, 1954, pp. 209–229, XP000901720.
Uber das 3,4–Dimethyl–1,2–Pyrazo–6,7–Pyron, das Lacton der Isopropylen–Methyl–Oxy–Pyrazol–Carbonsaure, Carl Bulow und Fritz Schaub, Berichte Der Deutschen Chemischen Gesellschaft, vol. 41, 1908, pp. 1945–1947, XP002135287; and.
Houben Weyl, Methoden der Orishenen Chemie, Falbe J., Teil 2, Band E5: Carbonsauren und Carbonsaurederivate, G. Thieme Verlag, Stuttgart, DE, XP002134923, p. 1175.

* cited by examiner

Primary Examiner—Paul J. Killos
Assistant Examiner—Héctor Reyes
(74) Attorney, Agent, or Firm—Michael W. Ferrell

(57) ABSTRACT

Process for the preparation of symmetrical diacylhydrazines having general formula (I): $R_1$—CO—NH—NH—CO—$R_1$ wherein $R_1$ represents a linear or branched $C_1$–$C_{18}$ alkyl group; a linear or branched $C_2$–$C_8$ alkoxyalkyl group; a $C_2$–$C_8$ cyanoalkyl group; a $C_5$–$C_8$ cycloalkyl group, said cycloalkyl group optionally containing a heteroatom selected from oxygen, nitrogen and sulfur; a $C_6$–$C_{18}$ aryl group; a $C_7$–$C_{20}$ arylalkyl group or alkylaryl group, said arylalkyl or alkylaryl groups optionally substituted with one or more hydroxyl groups, or with one or more linear or branched $C_1$–$C_8$ alkoxyl groups; comprising: (a) reacting an ester of a carboxylic acid having general formula (II): $R_1$—CO—$OR_2$ wherein $R_1$ has the same meanings defined above and $R_2$ represents a linear or branched $C_1$–$C_{18}$ alkyl group, with hydrazine, in its pure or hydrated state, obtaining a monoacylhydrazine having general formula (III): $R_1$—CO—NH—$NH_2$; (b) reacting the monoacylhydrazine having general formula (III) obtained in step (a), with a β-ketoester having general formula (IV): $R_3$—CO—$CH_2$—$COOR_4$ wherein $R_3$ represents a linear or branched $C_1$–$C_{18}$ alkyl group, or a $C_6$–$C_{18}$ aryl group and $R_4$ represents a linear or branched $C_1$–$C_{18}$ alkyl group, obtaining the desired symmetrical diacylhydrazine having general formula (I).

41 Claims, No Drawings

PROCESS FOR THE PREPARATION OF SYMMETRICAL DIACYLHYDRAZINES

The present invention relates to a process for the preparation of symmetrical diacylhydrazines.

More specifically, the present invention relates to a process for the preparation of symmetrical diacylhydrazines comprising the reaction of an ester with hydrazine, in its pure or hydrated state, to give a monoacylhydrazine which is subsequently reacted with a β-ketoester obtaining the desired symmetrical diacylhydrazine.

A further object of the present invention relates to the symmetrical diacylhydrazines obtained with the above process.

Various processes for the preparation of symmetrical diacylhydrazines are known in the art.

For example, the preparation of symmetrical diacylhydrazines can be easily effected by the reaction of hydrazine with acyl chlorides having general formula (Ia):

R—CO—Cl (Ia)

wherein R represents a linear or branched $C_1$–$C_{18}$ alkyl group, or an aryl group, operating according to the following reaction scheme (Scheme 1):

Scheme 1

2R—CO—Cl+1NH$_2$NH$_2$→1R—CO—NH—NH—CO—R+2H—Cl;

or by the reaction of the above hydrazine with anhydrides of carboxylic acids having general formula (Ib):

R—CO—O—CO—R (Ib)

wherein R has the same meanings described above, according to the following reaction scheme (Scheme 2):

Scheme 2

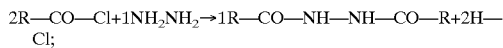
2R—CO—O—CO—R+1NH$_2$NH$_2$→1R—CO—NH—NH—CO—R+2R—COOH;

as described, for example, in Houben Weyl (1967) Band 10/2, pages 127–135; and in Patai (1970): "The Chemistry of Amides", Chapter 10, pages 533–535.

It is also known that, from the reaction of the acyl chlorides having general formula (Ia) described above, or anhydrides of carboxylic acids having general formula (Ib) described above, with hydrazine, operating with a molar ratio acyl chloride having general formula (Ia):hydrazine or anhydride of a carboxylic acid having general formula (Ib):hydrazine 1:1, according to the following reaction schemes (Scheme 3 and Scheme 4):

Scheme 3

1R—CO—Cl+1NH$_2$NH$_2$→1R—CO—NH—NH$_2$+1H—Cl;

Scheme 4

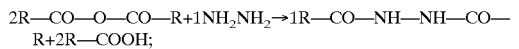
1R—CO—O—CO—R+1NH$_2$NH$_2$→1R—CO—NH—NH$_2$+1R—COOH;

monoacylhydrazines having general formula (IC) are obtained:

R—CO—NH—NH$_2$ (Ic)

wherein R has the same meanings described above.

It is also possible to prepare mixed diacylhydrazines by reacting the monoacylhydrazines having general formula (Ic) described above, with an acyl chloride having general formula (Id):

R'—CO—Cl (Id)

wherein R' has the same meanings as R described above, on the condition that R and R' are different from each other, according to the following reaction scheme (Scheme 5):

Scheme 5

1R—CO—NH—NH$_2$+1R'—CO—Cl→1R—CO—NH—NH—CO—R'+1H—Cl.

It is also known that the reaction of the hydrazine with esters of carboxylic acids having general formula (Ie):

R—CO—OR" (Ie)

wherein R has the same meanings described above and R" represents a linear or branched $C_1$–$C_{18}$ alkyl group, generally leads to the formation of monoacylhydrazines having general formula (Ic) described above, according to the following reaction scheme (Scheme 6)

Scheme 6

1R—CO—OR"+1NH$_2$NH$_2$→1R—CO—NH—NH$_2$+1R"—OH;

as described, for example, in Houben Weyl (1952) Band 8, page 676–679; and in Patai (1970): "The Chemistry of Amides", Chapter 10, pages 527–532. This reaction generally takes place using hydrated hydrazine (64% hydrazine; 36% water), in the presence of a polar solvent such as, for example, methanol, ethanol, dimethylformamide, water, etc. This hydrated hydrazine is a commonly used commercial product.

When the operation is carried out according to Scheme 6, the subsequent insertion of a second acyl group is generally very difficult and, when this insertion is possible, it is necessary to operate at high temperatures, for long reaction times and with the addition of acid catalysts.

In addition, in most cases, operating according to Scheme 6, the monoacylhydrazine which is formed by filtration or distillation of the reaction solvent and alcohol produced during the reaction, must be isolated. The formation of the symmetrical diacylhydrazine subsequently takes place by the elimination of a hydrazine mole from two moles of monoacylhydrazine having general formula (Ic) operating according to the following reaction scheme (Scheme 7):

Scheme 7

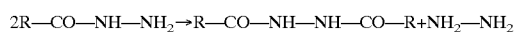
2R—CO—NH—NH$_2$→R—CO—NH—NH—CO—R+NH$_2$—NH$_2$ as described, for example, in Houben Weyl (1967) Band 10/2, pages 127–128.

Operating according to Scheme 7 above, in order to favour the progression of the reaction, the anhydrous hydrazine which is released, must be removed by distillation. As the distillation temperature of the anhydrous hydrazine is 113.5° C., it is necessary to use reaction temperatures of at least 150° C. and a high-boiling reaction solvent in order to be able to remove all the hydrazine released by the reaction, by means of distillation.

The elimination of the last percentages of hydrazine is very slow and consequently, owing to the high operating temperatures and long reaction times, numerous secondary products are formed which cause low yields and purities of the crystallized product obtained which rarely exceed 98%.

The undesired secondary products formed when operating according to Scheme 7 are tetrazine derivatives having the following general formulae (If) and (Ig)

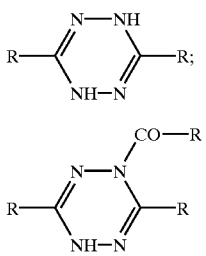

wherein R has the same meanings defined above.

Or, in order to obtain diacylhydrazines, the monoacylhydrazine having general formula (Ic) can be reacted with a mole of acyl chloride having general formula (Ia), or with a mole of an anhydride of a carboxylic acid having general formula (Ib), operating according to the following reaction schemes (Scheme 8 and Scheme 9):

Scheme 8

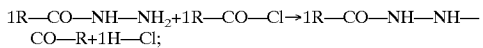

Scheme 9

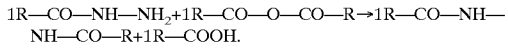

The Applicant has now found a process for the preparation of symmetrical diacylhydrazines comprising the reaction of an ester with hydrazine, in its pure or hydrated state, to give a monoacylhydrazine which is subsequently reacted with a β-ketoester obtaining the desired symmetrical diacylhydrazine, capable of overcoming the disadvantages of the known art.

The present invention therefore relates to a process for the preparation of symmetrical diacylhydrazines having general formula (I):

wherein:
  $R_1$ represents a linear or branched $C_1$–$C_{18}$ alkyl group; a linear or branched $C_2$–$C_8$ alkoxyalkyl group; a $C_2$–$C_8$ cyanoalkyl group; a $C_5$–$C_8$ cycloalkyl group, said cycloalkyl group optionally containing a heteroatom selected from oxygen, nitrogen and sulfur; a $C_6$–$C_{18}$ aryl group; a $C_7$–$C_{20}$ arylalkyl or alkylaryl group, said arylalkyl or alkylaryl groups optionally substituted with one or more hydroxyl groups, or with one or more linear or branched $C_1$–$C_8$ alkoxyl groups; comprising:
(A) reacting an ester of a carboxylic acid having general formula (II):

wherein $R_1$ has the same meanings defined above and $R_2$ represents a linear or branched $C_1$–$C_{18}$ alkyl group, with hydrazine, in its pure or hydrated state, obtaining a monoacylhydrazine having general formula (III):

(B) reacting the monoacylhydrazine having general formula (III) obtained in step (A), with a β-ketoester having general formula (IV):

wherein $R_3$ represents a linear or branched $C_1$–$C_{18}$ alkyl group, or a $C_6$–$C_{18}$ aryl group and $R_4$ represents a linear or branched $C_1$–$C_{18}$ alkyl group, obtaining the desired symmetrical diacylhydrazine having general formula (I).

Examples of $C_1$–$C_{18}$ alkyl groups are: methyl, ethyl, propyl, isopropyl, n-butyl, s-butyl, t-butyl, isobutyl, t-amyl, isoamyl, 2-ethylhexyl, n-octyl, 1,1,3,3-tetramethylbutyl, n-dodecyl, 1,1,7,7-tetramethyloctyl, n-octadecyl, etc.

Examples of $C_2$–$C_8$ alkoxyalkyl groups are: methoxyethyl, ethoxylethyl, ethoxypropyl, etc.

Examples of $C_2$–$C_8$ cyanoalkyl groups are: cyanomethyl, cyanoethyl, cyanopropyl, etc.

Examples of $C_5$–$C_8$ cycloalkyl groups, optionally containing a heteroatom, are: cyclopentyl, cyclohexyl, morpholinyl, piperidyl, etc.

Examples of $C_6$–$C_{18}$ aryl groups are: phenyl, naphthyl, anthracenyl, 2-hydroxyphenyl, etc.

Examples of $C_7$–$C_{20}$ arylalkyl or alkylaryl groups are: benzyl, 2-phenylethyl, 4-t-butylbenzyl, etc.

Examples of $C_1$–$C_8$ alkoxyl groups are: methoxyl, ethoxyl, propoxyl, n-butoxyl, etc.

In step (A) of the process object of the present invention the ester of carboxylic acid having general formula (II) and the hydrazine, in its pure or hydrated state, are used in molar ratios ranging from 1:1 to 1:6, preferably ranging from 1:1.1 to 1:4.

Step (A) is carried out in the presence of a polar organic solvent such as, for example, methanol, ethanol, n-butanol, dimethylformamide, water, or in the presence of a mixture of these polar organic solvents, at a temperature ranging from 10° C. to 150° C., preferably at a temperature ranging from 10° C. to 65° C. in the case of methanol, at a temperature ranging from 10° C. to 78° C. in the case of ethanol, at a temperature ranging from 10° C. to 100° C. in the case of water, butanol and dimethylformamide, for a time ranging from 0.5 hours to 15 hours, preferably from 1 hour to 10 hours.

Step (A) of the process object of the present invention can also be carried out in the presence of a mixture of the above polar organic solvents with hydrocarbon solvents such as, for example, toluene, xylene, etc., using a weight ratio polar organic solvent:hydrocarbon solvent ranging from 85:15 to 15:85, at a temperature ranging from 10° C. to 150° C., preferably from 50° C. to 100° C.

The monoacylhydrazine having general formula (III) obtained in step (A) is isolated, in its raw state, by means of two processes:
  by filtration of said monoacylhydrazine previously precipitated by cooling to a temperature ranging from 0° C. to 20° C.; or,
  by distillation of the hydrazine in excess and of the polar organic solvent which is partly or completely substituted with a higher-boiling hydrocarbon solvent, preferably toluene or xylene, without the need for crystallization.

When the isolation is carried out by distillation, the procedure is as follows:

distillation of the reaction solvent (polar organic solvent) and contemporaneous addition, by means of a drip funnel, of a hydrocarbon solvent in a quantity sufficient to allow the reaction mass to be stirred;

increase in the distillation temperature owing to the removal of the polar organic solvent, until the boiling point of the pure hydrocarbon solvent is reached and subsequent passage to step (B) described above, directly using the solution or suspension of the monoacylhydrazine having general formula (III) in the hydrocarbon solvent obtained at the end of the above distillation.

Alternatively, as already mentioned above, the monoacylhydrazine having general formula (III) obtained in step (A), can be isolated, in its raw state, by filtration of the precipitate obtained in step (A) by cooling to room temperature and subsequent washing with water to remove the excess hydrazine.

In step (B) of the process object of the present invention, the monoacylhydrazine having general formula (III) and the β-ketoester having general formula (IV) are used in molar ratios ranging from 1:0.2 to 1:1.1, preferably from 1:0.5 to 1:0.8.

Said step (B) is carried out in the presence of an organic solvent of the hydrocarbon type such as, for example, toluene, xylene, iso-octane, cyclohexane, methylcyclohexane, nonane, decane, undecane, decaline, etc., at the reflux temperature of the solvent ranging from 60° C. to 180° C., for a time ranging from 20 minutes to 15 hours, preferably from 20 minutes to 12 hours, obtaining the desired symmetrical diacylhydrazine having general formula (I), an alkyl-pyrazolone or an aryl-pyrazolone having general formula (V), an alcohol having general formula (VI) and water as indicated in the following reaction scheme:

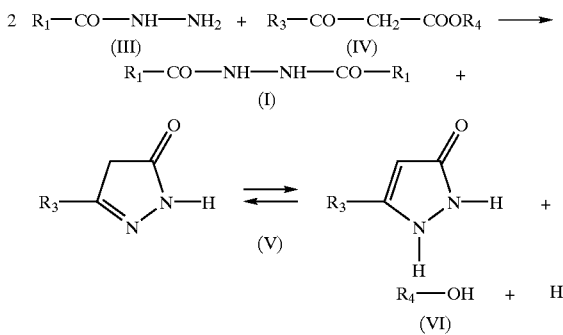

wherein $R_1$, $R_3$ and $R_4$ have the same meanings described above.

The reaction water which is formed in step (B) is separated by azeotropic distillation.

The above organic solvent of the hydrocarbon type is added operating as follows:

when the monoacyihydrazine having general formula (III) is isolated by filtration, it is added directly to the raw monoacylhydrazine obtained;

when the monoacylhydrazine having general formula (III) is isolated by distillation, it is added during the distillation of the polar organic solvent (as already described above).

A precipitate is formed in the reaction mass, during step (B) above, which consists of:

about 10%–40% of alkyl-pyrazolone or aryl-pyrazolone having general formula (V); and about 60%–90% of symmetrical diacylhydrazine having general formula (I).

The reaction yield is usually very high and there is no formation of undesired secondary products such as, for example, the tetrazine compounds having general formula (If) and (Ig) described above.

The above reaction mass can be directly subjected to the treatment described hereunder to separate the symmetrical diacylhydrazine having general formula (I) from the alkyl-pyrazolone or aryl-pyrazolone having general formula (V).

Or, the above precipitate can be isolated from the reaction mass, after this is cooled to 0° C.–50° C., by means of filtration and drying in an oven at 50° C.–100° C., preferably 70° C.–90° C., under vacuum. In this case, a hydrocarbon solvent immiscible in water such as, for example, toluene, xylene, etc. is added to the precipitate thus isolated, which is then subjected to the treatment described hereunder to separate the symmetrical diacylhydrazine having general formula (I) from the alkyl-pyrazolone or aryl-pyrazolone having general formula (V).

The separation of the symmetrical diacylhydrazine having general formula (I) from the alkyl-pyrazolone or aryl-pyrazolone having general formula (V), can be effected by means of one or more hot aqueous washings, at a temperature ranging from 85° C. to 125° C., at a pressure ranging from 1 kg/cm² to 4 kg/cm²: the alkyl-pyrazolone or aryl-pyrazolone passes into the aqueous phase in which it is soluble under heat. If the passage of the alkyl-pyrazolone or aryl-pyrazolone into the hot aqueous phase is insufficient, it is possible to carry out an additional washing with a diluted acid solution, at a concentration ranging from 2% to 10%, preferably from 4% to 8%, of a strong inorganic acid such as, for example, hydrochloric acid or sulfuric acid, operating at the same temperature and pressure at which the above hot aqueous washing is effected.

Alternatively, the separation of the symmetrical diacylhydrazine having general formula (I) from the alkyl-pyrazolone or aryl-pyrazolone having general formula (V) can be effected by means of a washing with a diluted acid solution, at a concentration ranging from 2% to 10%, preferably from 4% to 8%, of a strong inorganic acid such as, for example, hydrochloric acid or sulfuric acid, at a temperature ranging from 80° C. to 90° C., preferably from 84° C. to 86° C., at atmospheric pressure. To favour this washing, a $C_4$–$C_5$ alcohol can be optionally added to improve the solubility of the symmetrical diacylhydrazine in the organic phase. A hot aqueous washing is then effected at the same temperature as the above acid washing, at atmospheric pressure.

At the end of the above washings, during which the alkyl-pyrazolone or aryl-pyrazolone having general formula (V) is extracted from the organic phase, this phase, containing only the symmetrical diacylhydrazine having general formula (I), is anhydrified by distillation, heating to 100° C.–110° C., preferably 100° C.–105° C. The symmetrical diacylhydrazine having general formula (I) is subsequently crystallized by cooling to 50° C.–10° C., preferably 20° C.–0° C., and is then filtered, washed with the same reaction solvent and dried in an oven at 50° C.–100° C., preferably 70° C.–90° C., under vacuum.

Step (B) above, when the monoacylhydrazine having general formula (III) is isolated in its raw state by filtration, can also be carried out in the presence of a polar organic solvent such as, for example, butanol, propanol, amyl alcohol, dimethylformamide, etc. In this case, during the reaction which is carried out at reflux temperature, there is no separation of the reaction water and the reaction mass proves to consist of a solution without a precipitate. Upon subsequent cooling to 0° C., the symmetrical diacylhydrazine having general formula (I) and the alkyl-pyrazolone or aryl-pyrazolone having general formula (V) precipitate: the precipitate is filtered and dried in an oven at 50° C.–100° C., preferably 70° C.–90° C., under vacuum. A hydrocarbon solvent immiscible with water such as, for example toluene, xylene, etc. is added to the precipitate thus isolated, which is then subjected to the treatment described above to separate the symmetrical diacylhydrazine having general formula (I) from the alkyl-pyrazolone or aryl-pyrazolone having general formula (V).

The symmetrical diacylhydrazine having general formula (I) obtained with the process object of the present invention, has a purity of over 98.0%. The reaction yield is over 85% when it refers to the quantity of monoacylhydrazine having general formula (III) used in step (B) of the above process and over 70% when it refers to the quantity of ester having general formula (II) used in step (A) of the above process.

The hydrazine, in its pure or hydrated state, used in step (A) of the process object of the present invention, is a product which is commercially available.

Examples of esters having general formula (II) which can be used in step (A) of the process object of the present invention are: methyl or ethyl acetate, methyl or ethyl butyrate, methyl or ethyl cyanoacetate, methyl or ethyl propionate, methyl or ethyl octanoate, methyl or ethyl benzoate, methyl or ethyl dodecanoate, methyl or ethyl salicylate, methyl 4-methyl-benzoate, ethyl isoamylacetate, ethyl phenylacetate, methyl 3-(3,5-di-t-butyl-4-hydroxyphenyl)-propionate, etc.

The above esters having general formula (II) are commercially available, or they can be prepared according to processes known in the art.

Examples of monoacylhydrazines having general formula (III), obtained in step (A) of the process object of the present invention, are: acetylhydrazine, cyanoacetylhydrazine, butyrylhydrazine, propionylhydrazine, n-octanoylhydrazine, isoamylacetylhydrazine, glycolylhydrazine, benzoylhydrazine, 4-methylbenzoylhydrazine, salicyloylhydrazine, dodecanoylhydrazine, phenylacetylhydrazine, 3-(3,5-di-t-butyl-4-hydroxyphenyl)propionylhydrazine, etc.

The above monoacylhydrazines having general formula (III) can also be commercially available: in this case, step (A) of the process object of the present invention is not effected.

A further object of the present invention therefore relates to a process for the preparation of symmetrical diacylhydrazines having general formula (I) described above, comprising the reaction of a monoacylhydrazine having general formula (III) described above, with a β-ketoester having general formula (IV) described above, operating according to what is described for step (B).

Examples of β-ketoesters having general formula (IV) which can be used in step (B) of the process object of the present invention, are: methyl acetoacetate, ethyl acetoacetate, t-butyl acetoacetate, ethyl benzoyl acetate, etc.

The above β-ketoesters having general formula (IV) are commercially available.

Specific examples of symmetrical diacylhydrazines having general formula (I) which can be obtained with the process object of the present invention, but which in no way limit its scope, are: 1,2-di-propionylhydrazine, 1,2-di-butyrylhydrazine, 1,2-di-isoamylacetylhydrazine, 1,2-di-glycolylhydrazine, 1,2-di-acetylhydrazine, 1,2-di-n-octanoylhydrazine, 1,2-di-benzoylhydrazine, 1,2-di-salicyloylhydrazine, 1,2-di-dodecanoylhydrazine, 1,2-diphenylacetylhydrazine, 1,2-di-p-toluoylhydrazine, N,N'-bis-[3-(3,5-di-t-butyl-4-hydroxyphenyl)propionyl] hydrazine, etc.

Some illustrative examples are provided for a better understanding of the present invention and for its embodiment but in no way limit the scope of the invention itself.

EXAMPLE 1

Preparation of N,N'-bis-[3-(3,5-di-t-butyl-4-hydroxyphenyl)propionyl]hydrazine (A) Preparation of 3-(3,5-di-t-butyl-hydroxyphenyl) propionylhydrazine 60 g of methanol, 30 g of toluene, 58.5 g (0.2 moles) of methyl 3-(3,5-di-t-butyl-4-hydroxyphenyl)propionate and 20 g (0.4 moles) of hydrated hydrazine at 64% are charged into a 250 ml four-necked flask equipped with a mechanical stirrer, thermometer and reflux condenser connected to a phase separator: the resulting mixture is kept under stirring and reflux heated to 72° C. for 9 hours and the conversion of the ester to monoacylhydrazine proves to be over 96%.

A further 50 g of toluene are added to the above mixture. The recycling valve from the condenser to the reactor is then closed and the solvent is distilled. During the distillation, the temperature gradually rises, over a period of about 30 minutes, from 72° C. to 79° C. and, at this stage, the distillate prevalently consists of methanol (first fraction) and is limpid and colourless. As the distillation proceeds, the temperature rises again and, at about 80° C.–85° C., after a further 30 minutes, the distillate separates into two phases: a lower phase consisting of water, methanol and hydrazine (second fraction), and an upper phase consisting of a solution of toluene and methanol (third fraction). As the distillation proceeds further, and as the temperature rises, both of the above phases are discharged, for a certain period, until, at about 100° C., the recycling valve from the condenser to the reactor is reopened and the lower phase continues to be discharged whereas the upper phase, prevalently consisting of toluene, is recycled to the reactor.

A further 50 g of toluene are slowly added in portions, without letting the reaction mass cool and the distillation is continued until a temperature of 113° C.–115° C. is reached in the reactor: the overall duration of the distillation is 3 hours and 30 minutes.

The fractions obtained from the above distillation prevalently consisting: the first of methanol, the second of the lower phase and the third of the upper phase (as described above), are joined, obtaining a mixture consisting of 25 g of organic phase (methanol and toluene) and 68 g of aqueous phase (water, methanol and hydrazine). This mixture is eliminated.

The residue in the reactor, on the contrary, prevalently consisting of a toluene solution of monoacylhydrazine without hydrazine and water, is subjected to the subsequent reaction step (B).

(B) Preparation of N,N'-bis[3-(3,5-di-t-butyl-4-hydroxyphenyl)propionyl]hydrazine 12 g (0.095 moles) of methyl acetoacetate are added to the distillation residue obtained as described above, consisting of a limpid toluene solution containing 56.1 g (0.19 moles) of 3-(3,5-di-t-butyl-4-hydroxyphenyl)propionylhydrazine, maintained at reflux temperature equal to 115° C. During this addition, there is the immediate separation of reaction water by means of azeotropic distillation whereas the toluene is recycled to the reactor and, after about 30 minutes, a white precipitate is formed.

The reaction progress is followed by high pressure liquid chromatography (HPLC).

The reaction finishes after about 4 hours of reflux heating at 115° C. during which the starting 3-(3,5-di-t-butyl-4-hydroxyphenyl)propionylhydrazine is completely used up with the formation of N,N'-bis[3-(3,5-di-t-butyl-4-hydroxyphenyl)propionyl]hydrazine and 3-methyl-5-pyrazol-one: at the end of the reaction the quantity of reaction water separated by azeotropic distillation is equal to 2 ml.

The reaction mass is subjected to a washing with 30 g of amyl alcohol and 20 g of an aqueous solution of hydrochloric acid at 7.5%, operating at a temperature equal to 85° C. and at atmospheric pressure. During this washing, the 3-methyl-5-pyrazolone passes in solution into the aqueous phase in the form of hydrochloride whereas the N,N'-bis[3-(3,5-di-t-butyl-4-hydroxyphenyl)propionyl]hydrazine remains dissolved in the toluene phase. The aqueous phase is separated and a further two hot washings are effected, each with 30 g of water, operating at a temperature equal to 85° C.

The 3-methyl-5-pyrazolone which, as described above, was eliminated from the toluene solution as an aqueous solution of its hydrochloride, is isolated and characterized by precipitation, after neutralization with sodium hydroxide at 5%, filtration and drying, obtaining 7.5. g of 98% pure pyrazolone. The recovery yield of 3-methyl-5-pyrazolone is equal to 76.4%.

The 3-methyl-5-pyrazolone was characterized by comparing its NMR spectra (Bruker AC 200 spectrometer) with the spectra of a commercial 3-methyl-5-pyrazolone (produced by Aldrich Chimica).

The toluene phase containing N,N'-bis[3-(3,5-di-t-butyl-4-hydroxyphenyl)propionyl]hydrazine is anhydrified by means of azeotropic distillation, by heating to 105° C. On cooling this toluene solution to 90° C., the crystallization of said hydrazine begins and is completed by cooling to 20° C. in 6 hours.

The N,N'-bis[3-(3,5-di-t-butyl-4-hydroxyphenyl)propionyl]hydrazine is filtered, washed with 40 g of toluene and dried under vacuum (20 mm/Hg), at 80° C. for 5 hours, obtaining:

symmetrical diacylhydrazine: 46.5 g;
yield[1]: 88.5%;
yield[2]: 84.1%;
purity (HPLC): >99%;
melting point: 229° C.

(1): yield referring to the quantity of 3-(3,5-di-t-butyl-4-hydroxyphenyl)propionylhydrazine charged;
(2): yield referring to the quantity of methyl 3-(3,5-di-t-butyl-4-hydroxyphenyl)propionate charged.

The mass spectrum carried out with an LCQ Finnigan spectrometer and FT-IR spectrum carried out with a Nicolet Magna IR 550 spectrophotometer, are in accordance with the structure.

EXAMPLE 2

Preparation of N,N'-bis-([3-(3,5-di-t-butyl-4-hydroxyphenyl)propionyl]hydrazine (A) Preparation of 3-(3,5-di-t-butyl-4-hydroxyphenyl)-propionylhydrazine 160 g of methanol and 117 g (0.4 moles) of methyl 3-(3,5-di-t-butyl-4-hydroxyphenyl)propionate are charged into a 500 ml four-necked flask equipped with a mechanical stirrer, thermometer and reflux condenser connected to a phase separator, and maintained under stirring: the mixture is heated to 45° C.–50° C. and 80.1 g (1.6 moles) of hydrated hydrazine at 64% are gradually added. The resulting mixture is maintained under stirring and reflux heated to 72° C. for 6.5 hours and the conversion of the ester to monoacylhydrazine proves to be over 98%. After 6.5 hours there is the formation of a little precipitate consisting of monoacylhydrazine.

The mixture is slowly cooled to 50° C., 10 g of water are added and it is finally cooled to 20° C. in 8 hours and filtered obtaining a cake which is washed with 150 g of water to remove the excess hydrazine. This humid cake is equal to 167.1 g with a dry residue of 68.7% corresponding to 114.8 g at 100%.

The gas-chromatographic purity of a small portion dried aside at 90° C. gave a value equal to 99.4%.

The reaction yield, referring to the quantity of methyl 3-(3,5-di-t-butyl-4-hydroxyphenyl)propionate charged, is equal to 98.1%.

(B) Preparation of N,N'-bis[3-(3,5-di-t-butyl-4-hydroxyphenyl)propionyl]hydrazine 75 g of toluene, 42.8 g humid at 68.4% of dry residue of 3-(3,5-di-t-butyl-4-hydroxyphenyl)propionylhydrazine corresponding to 29.24 g (0.1 moles) at 100% of dry residue, obtained as described above in step (A) and 5.81 g (0.05 moles) of methyl acetoacetate, are charged into a 250 ml four-necked flask equipped with a mechanical stirrer, thermometer and reflux condenser connected to a phase separator, and maintained under stirring.

The resulting mixture consisting of a suspension, is reflux heated (115° C.) until the complete dissolution of the monoacylhydrazine in the toluene solution; the water present at the beginning in the humid monoacylhydrazine is separated from the distillate collector, together with the reaction water, whereas the toluene is recycled to the reactor. After about 30 minutes, a white precipitate is formed.

The reaction progress is followed by high pressure liquid chromatography (HPLC).

The reaction finishes after about 4 hours of the above reflux heating (115° C.), during which the starting 3-(3,5-di-t-butyl-4-hydroxyphenyl)propionylhydrazine is completely used up with the formation of N,N'-bis[3-(3,5-di-t-butyl-4-hydroxyphenyl)propionyl]hydrazine and 3-methyl-5-pyrazolone.

25 g of water are added to the reaction mass and a washing is effected at 120° C. under a maximum pressure of 3 kg/cm$^2$. During this washing, the 3-methyl-5-pyrazolone passes in solution into the aqueous phase whereas the N,N'-bis[3-(3,5-di-t-butyl-4-hydroxyphenyl)propionyl]hydrazine remains dissolved in the toluene phase. The aqueous phase is separated and a second washing is carried out with a further 25 g of water and a third washing with an aqueous solution at 4% of hydrochloric acid, operating at the same temperature and pressure as the above hot aqueous washing, to eliminate the last traces of 3-methyl-5-pyrazolone from the toluene phase.

The toluene phase thus obtained is cooled to 95° C. and anhydrified, by means of azeotropic distillation, by heating to 105° C. after re-establishing the system at atmospheric pressure. The temperature of the toluene phase is brought to 90° C. thus starting the crystallization of the N,N'-bis[3-(3,5-di-t-butyl-4-hydroxyphenyl)propionyl]hydrazine which is completed by cooling to 20° C. over a period of 6 hours.

The N,N'-bis[3-(3,5-di-t-butyl-4-hydroxyphenyl)propionyl]hydrazine is filtered, washed with 20 g of toluene and dried under vacuum (20 mm/Hg), at 80° C. for 5 hours, obtaining:

symmetrical diacylhydrazine: 24.9 g;
yield[1]: 90.0%;
yield[2]: 88.3%;
purity (HPLC): >99%;
melting point: 229° C.

(1): yield referring to the quantity of 3-(3,5-di-t-butyl-4-hydroxyphenyl)propionylhydrazine charged;
(2): yield referring to the quantity of methyl 3-(3,5-di-t-butyl-4-hydroxyphenyl)propionate charged.

EXAMPLE 3

Preparation of N,N'-bis-[3-(3,5-di-t-butyl-4-hydroxy-phenyl)propionyl]hydrazine 75 g of toluene, 29.24 g (0.1 moles) of anhydrous 3-(3,5-di-t-butyl-4-hydroxyphenyl)propionylhydrazine (obtained as described above in step (A) of Example 2 and subjected to drying in an oven) and 6.5 g (0.05 moles) of ethyl acetoacetate are charged into a 250 ml four-necked flask equipped with a mechanical stirrer, thermometer and reflux condenser connected to a phase separator, and maintained under stirring.

The same procedure is adopted as in step (B) of Example 2 and the reaction finishes after 4.5 hours of reflux heating (115° C.). The reaction water which is separated is about 0.9 ml.

40 g of toluene are added to the reaction mass, the mixture is cooled to 50° C. and the precipitate which consists of a raw mixture of N,N'-bis[3-(3,5-di-t-butyl-4-hydroxyphenyl)propionyl]hydrazine and 3-methyl-5-pyrazolone is filtered and washed twice with 30 g of toluene: the precipitate thus obtained is dried, under vacuum, at 80° C., for 5 hours obtaining 30.7 g of a mixture containing about 82% of N,N'-bis-[3(3,5-di-t-butyl-4-hydroxyphenyl)propionyl]-hydrazine and 18% of 3-methyl-4-pyrazolone: the two compounds were characterized operating as described in Example 1.

The yield to N,N'-bis-[3-(3,5-di-t-butyl-4-hydroxyphenyl)propionyl]hydrazine proves to be >90% with respect to the 3-(3,5-di-t-butyl-4-hydroxyphenyl)propionylhydrazine charged.

EXAMPLE 4

Preparation of N,N'-bis-[3-(3,5-di-t-butyl-4-hydroxyphenyl)propionyl]hydrazine.

80 g of toluene, 58.48 g (0.2 moles) of anhydrous 3-(3,5-di-t-butyl-4-hydroxyphenyl)propionylhydrazine (obtained as described above in step (A) of Example 2 and subjected to drying in an oven) and 21.35 g (0.1 moles) of ethyl benzoylacetate are charged into a 250 ml four-necked flask equipped with a mechanical stirrer, thermometer and reflux condenser connected to a phase separator, and maintained under stirring.

The same procedure is adopted as in step (B) of Example 2 and the reaction is complete after 12 hours of reflux heating (115° C.). The reaction water which is separated is about 2 ml.

In this case, the product which is formed together with the N,N'-bis[3-(3,5-di-t-butyl-4-hydroxyphenyl)propionyl]hydrazine is 3-phenyl-5-pyrazolone (6.2 g; melting point: 242° C.) which is isolated and characterized by precipitation of the acid washing after neutralization with soda at 3% and analyzed by means of HPLC/MASS analysis; the NMR analysis is also in accordance with the structure.

The following results are obtained from the above reaction:

symmetrical diacylhydrazine: 49.0 g;

yield[(1)]: 89.0%;

purity (HPLC): >98%;

melting point: 227° C.

(1): yield referring to the quantity of 3-(3,5-di-t-butyl-4-hydroxyphenyl)propionylhydrazine charged.

EXAMPLE 5

Preparation of N,N'-bis-[3-(3,5-di-t-butyl-4-hydroxyphenyl)propionyl]hydrazine 70 g of n-butanol, 29.24 g (0.1 moles) of anhydrous 3-(3,5-di-t-butyl-4-hydroxyphenyl)propionylhydrazine (obtained as described above in step (A) of Example 2 and subjected to drying in an oven) and 5.8 g (0.05 moles) of methyl acetoacetate are charged into a 250 ml four-necked flask equipped with a mechanical stirrer, thermometer and reflux condenser connected to a phase separator, and maintained under stirring.

The same procedure is adopted as in step (B) of Example 2 with the difference that, in this case, under reflux conditions (118° C.) there is no separation of water and the reaction mass consists of a limpid, light-yellow solution.

The reaction is interrupted after 4 hours of reflux heating and, after cooling to 0° C., the N,N'-bis[3-(3,5-di-t-butyl-4-hydroxyphenyl)propionyl]hydrazine and 3-methyl-5-pyrazolone precipitate, obtaining 28 g of a solid which is filtered, dried and analyzed by means of HPLC/MASS analysis which confirms the structure of the products of which the solid is formed.

This solid consists of 86% of N,N'-bis[3-(3,5-di-t-butyl-4-hydroxyphenyl)propionyl]hydrazine (yield >85% referring to the quantity of 3-(3,5-di-t-butyl-4-hydroxyphenyl)propionylhydrazine charged) and 14% of 3-methyl-5-pyrazolone.

EXAMPLE 6

Preparation of 1,2-dibenzoylhydrazine 100 g of toluene, 27.20 g (0.2 moles) of benzoylhydrazine (commercial product of Aldrich Chimica) and 11.6 g (0.1 moles) of methyl acetoacetate are charged into a 250 ml four-necked flask equipped with a mechanical stirrer, thermometer and reflux condenser connected to a phase separator, and maintained under stirring.

The mixture obtained is reacted by heating to reflux temperature (115° C.) for 3 hours.

The reaction water, about 2 ml, is separated by azeotropic distillation whereas the toluene is recycled to the reactor.

During the reaction there is the complete dissolution of all the components and, after about 1 hour, a precipitate is formed.

The starting benzoylhydrazine is completely used up with the formation of a mixture comprising 1,2-dibenzoylhydrazine and 3-methyl-5-pyrazolone. This mixture is washed with 50 g of amyl alcohol and 20 g of an aqueous solution of hydrochloric acid at 7.5%, at 85° C. and at atmospheric pressure. During the washing the 3-methyl-pyrazolone passes in solution into the aqueous phase whereas the 1,2-dibenzoylhydrazine remains partly dissolved and partly suspended in the toluene phase.

The limpid aqueous phase is separated, whereas the toluene phase is subjected to two washings with 20 g of water each, at 85° C. and at atmospheric pressure, to eliminate any traces of acidity present.

The toluene phase is then anhydrified by means of azeotropic distillation, by heating so as to reach a temperature of 105° C. Upon further cooling of the toluene phase to 20° C., in 4 hours, the precipitation of 1,2-dibenzoylhydrazine is completed.

The 1,2-dibenzoylhydrazine is filtered, washed with 40 g of toluene and dried under vacuum (20 mm/Hg) at 80° C. for 4 hours, obtaining:

symmetrical diacylhydrazine: 22.0 g;
yield[(1)]: 91.6%;
purity (HPLC): >98%;
melting point: 236.8° C.

(1): yield referring to the quantity of benzoylhydrazine charged.

EXAMPLE 7

Preparation of 1,2-di-n-octanoylhydrazine 100 g of toluene, 39.50 g (0.2 moles) of n-octanoylhydrazine at 80% (commercial product of Aldrich Chimica) and 11.6 g (0.1 moles) of methyl acetoacetate are charged into a 250 ml four-necked flask equipped with a mechanical stirrer, thermometer and reflux condenser connected to a phase separator, and maintained under stirring.

The same procedure is adopted as in Example 6 and washings are carried out with an aqueous solution of hydrochloric acid at 7.5%, at 85° C. and atmospheric pressure, obtaining 1,2-di-n-octanoylhydrazine and 3-methyl-5-pyrazolone.

The 1,2-di-n-octanoylhydrazine is filtered, washed with 40 g of toluene and dried under vacuum (20 mm/Hg) at 80° C. for 4 hours, obtaining:

symmetrical diacylhydrazine: 25.7 g;
yield[(1)]: 90.0%;
purity (HPLC): >99%;
melting point: 155.4° C.

(1): yield referring to the quantity of n-octanoylhydrazine charged.

The mass spectrum is in accordance with the structure.

What is claimed is:

1. A process for the preparation of symmetrical diacylhydrazines having general formula (I):

$$R_1—CO—NH—NH—CO—R_1 \quad (I)$$

wherein:

$R_1$ represents a linear or branched $C_1$–$C_{18}$ alkyl group; a linear or branched $C_2$–$C_8$ alkoxyalkyl group; a $C_2$–$C_8$ cyanoalkyl group; a $C_5$–$C_8$ cycloalkyl group, said cycloalkyl group optionally containing a heteroatom selected from oxygen, nitrogen and sulfur; a $C_6$–$C_{18}$ aryl group; or a $C_7$–$C_{20}$ arylalkyl or alkylaryl group, said arylalkyl or alkylaryl groups optionally substituted with one or more hydroxyl groups, or with one or more linear or branched $C_1$–$C_8$ alkoxyl groups; comprising the following steps:

(A) reacting an ester of a carboxylic acid having general formula (II):

$$R_1—CO—OR_2 \quad (II)$$

wherein $R_1$ has the same meanings defined above and $R_2$ represents a linear or branched $C_1$–$C_{18}$ alkyl group, with hydrazine, in its pure or hydrated state, obtaining a monoacylhydrazine having general formula (III):

$$R_1—CO—NH—NH_2 \quad (III);$$

(B) reacting the monoacylhydrazine having general formula (III) obtained in step (A), with a β-ketoester having general formula (IV):

$$R_3—CO—CH_2—COOR_4 \quad (IV)$$

wherein $R_3$ represents a linear or branched $C_1$–$C_{18}$ alkyl group, or a $C_6$–$C_{18}$ aryl group and $R_4$ represents a linear or branched $C_1$–$C_{18}$ alkyl group, obtaining the desired symmetrical diacylhydrazine having general formula (I); the monoacylhydrazine having general formula (III) and the β-ketoester having general formula (IV) being used in molar ratios ranging from 1:0.5 to 1:0.8; and said step (B) being carried out in the presence of a hydrocarbon solvent at the reflux temperature of the solvent ranging from 60° C. to 180° C., for a time ranging from 20 minutes to 15 hours, obtaining the desired symmetrical diacylhydrazine having general formula (I), an alkyl-pyrazolone or an aryl-pyrazolone having general formula (V), an alcohol having general formula (VI) and water as indicated in the following reaction scheme:

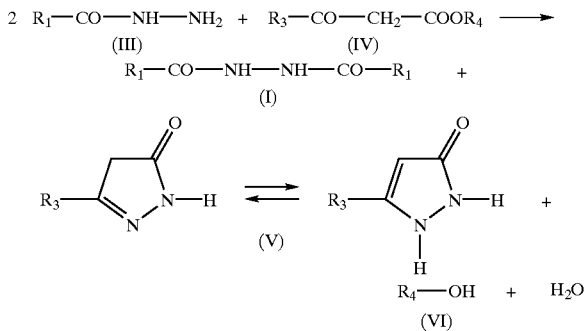

wherein $R_1$, $R_3$ and $R_4$ have the same meanings defined above.

2. The process according to claim 1, wherein the $C_1$–$C_{18}$ alkyl groups are: methyl, ethyl, propyl, isopropyl, n-butyl, s-butyl, t-butyl, isobutyl, t-amyl, isoamyl, 2-ethylhexyl, n-octyl, 1,1,3,3-tetramethylbutyl, n-dodecyl, 1,1,7,7-tetramethyloctyl, n-octadecyl.

3. The process according to claim 1, wherein the $C_2$–$C_8$ alkoxyalkyl groups are: methoxyethyl, ethoxyethyl, ethoxypropyl.

4. The process according to claim 1, wherein the $C_2$–$C_8$ cyanoalkyl groups are: cyanomethyl, cyanoethyl, cyanopropyl.

5. The process according to claim 1, wherein the $C_5$–$C_8$ cycloalkyl groups, optionally containing a heteroatom, are: cyclopentyl, cyclohexyl, morpholinyl, piperidyl.

6. The process according to claim 1, wherein the $C_6$–$C_{18}$ aryl groups are: phenyl, naphthyl, anthracenyl, 2-hydroxyphenyl.

7. The process according to claim 1, wherein the $C_7$–$C_{20}$ arylalkyl or alkylaryl groups are: benzyl, 2-phenyl-ethyl, 4-t-butylbenzyl.

8. The process according to claim 1, wherein the $C_1$–$C_8$ alkoxyl groups are: methoxyl, ethoxyl, propoxyl, n-butoxyl.

9. The process according to claim 1, wherein in step (A) the ester of carboxylic acid having general formula (II) and the hydrazine, in its pure or hydrated state, are used in molar ratios ranging from 1:1 to 1:6.

10. The process according to claim 9, wherein the ester of carboxylic acid having general formula (II) and the hydrazine, in its pure or hydrated state, are used in molar ratios ranging from 1:1.1 to 1:4.

11. The process according to claim 1, wherein step (A) is carried out in the presence of a polar organic solvent or water, or a mixture of compounds selected from the group consisting of polar organic solvents and water, at a temperature ranging from 10° C. to 150° C., for a time ranging from 0.5 hours to 15 hours.

12. The process of claim 11, wherein said polar organic solvent is methanol, ethanol, n-butanol or dimethylformamide.

13. The process according to claim 12, wherein step (A) is carried out at a temperature ranging from 10° C. to 65° C. in the case of methanol, at a temperature ranging from 10° C. to 78° C. in the case of ethanol, at a temperature ranging from 10° C. 100° C. in the case of water, butanol and dimethylformamide, for a time ranging from 0.5 hours to 15 hours.

14. The process according to claim 11 or 13, wherein step (A) is carried out for a time ranging from 1 hour to 10 hours.

15. The process according to claim 1, wherein step (A) is carried out in the presence of a mixture of compounds selected from the group consisting of polar organic solvents and water with a hydrocarbon solvent using a weight ratio of polar organic solvent and water:hydrocarbon solvent ranging from 85:15 and 15:85, at a temperature ranging from 10° C. to 1.50° C.

16. The process according to claim 15, wherein step (A) is carried out at a temperature ranging from 50° C. to 100° C.

17. The process of claim 15, wherein said hydrocarbon solvent is toluene or xylene.

18. The process according to claim 1, wherein the monoacylhydrazine having general formula (III) obtained in step (A) is isolated, in its raw state, by means of two processes:
 by filtration of said monoacylhydrazine previously precipitated by cooling to a temperature ranging from 0° C. to 20° C.; or,
 by distillation of the hydrazine in excess and of the polar organic solvent which is partly or completely substituted with a higher-boiling hydrocarbon solvent, such as toluene or xylene, without the need for crystallization.

19. The process according to claim 18, wherein the isolation takes place by distillation and the following procedure is adopted:
 distillation of the reaction solvent (polar organic solvent) and contemporaneous addition, by means of a drip funnel, of a hydrocarbon solvent in a quantity sufficient to allow the reaction mass to be stirred;
 increase in the distillation temperature owing to the removal of the polar organic solvent, until the boiling point of the pure hydrocarbon solvent is reached and subsequent passage to step (B) directly using the solution or suspension of the monoacylhydrazine having general formula (III) in the hydrocarbon solvent obtained at the end of the above distillation.

20. The process according to claim 18, wherein the monoacylhydrazine having general formula (III) obtained in step (A), isolated, in its raw state, by means of filtration of the precipitate obtained in the above step (A) by cooling to room temperature and subsequent washing with water to remove the excess hydrazine.

21. The process according to claim 1, wherein said reaction time of step (B) ranges from 20 minutes to 12 hours.

22. The process according to claim 1, wherein said hydrocarbon solvent is added operating as follows:
 when the monoacylhydrazine having general formula (III) is isolated by filtration, it is added directly to the raw monoacylhydrazine obtained;
 when the monoacylhydrazine having general formula (III) is isolated by distillation, it is added during the distillation of the polar organic solvent.

23. The process according to claims 1, wherein in the reaction mass, during step (B), there is the formation of a precipitation consisting of:
 about 10%–40% of alkyl-pyrazolone or aryl-pyrazolone having general formula (V); and
 about 60%–90% of symmetrical diacylhydrazine having general formula (I).

24. The process according to claim 23, wherein the reaction mass is directly subjected to one or more hot aqueous washings, at a temperature ranging from 85° C. to 125° C., at a pressure ranging from 1 kg/cm$^2$ and 4 kg/cm$^2$ to separate the symmetrical diacylhydrazine having general formula (I) from the alkyl-pyrazolone or from the aryl-pyrazolone having general formula (V).

25. The process according to claim 24, wherein an additional washing is carried out with a diluted acid solution, at a concentration ranging from 2% to 10%, of a strong inorganic acid operating at the same temperature and pressure as the above hot aqueous washing.

26. The process of claim 25, wherein said strong inorganic acid is hydrochloric acid or sulfuric acid.

27. The process according to claim 24, wherein the separation of the symmetrical diacylhydrazine having general formula (I) from the alkyl-pyrazolone or aryl-pyrazolone having general formula (V) is carried out by means of a washing with a diluted acid solution, at a concentration ranging from 2% to 10%, of a strong inorganic acid, at a temperature ranging from 80° C. to 90° C. and at atmospheric pressure.

28. The process according to claim 27, wherein, in order to favour the above washing, a $C_4$–$C_5$ alcohol is added and a hot aqueous washing is subsequently effected at the same temperature as the above acid washing, at atmospheric pressure.

29. The process of claim 27, wherein said strong inorganic acid is hydrochloric acid or sulfuric acid.

30. The process according to claim 23, wherein at the end of the above washings, the organic phase, containing the symmetrical diacylhydrazine having general formula (I) alone, is anhydrified by means of distillation, by heating to 100° C.–110° C., and subsequently cooled to 50° C.–10° C. obtaining the crystallized symmetrical diacylhydrazine having general formula (I), which is filtered, washed with the same reaction solvent and dried in an oven at 50° C.–100° C.

31. The process according to claim 23, wherein the above precipitate is isolated, after cooling the reaction mass to 0° C.–50° C., by filtration and drying in an oven at 50° C.–100° C., under vacuum.

32. The process according to claim 31, wherein a hydrocarbon solvent immiscible with water is added to the precipitate obtained, and the separation of the symmetrical diacylhydrazine having general formula (I) from the alkyl-pyrazolone or aryl-pyrazolone having general formula (V), is effected by means of one or more hot aqueous washings, at a temperature ranging from 85° C. to 125° C., at a pressure ranging from 1 kg/cm$^2$ to 4 kg/cm$^2$.

33. The process of claim 32, wherein said hydrocarbon solvent is toluene or xylene.

34. The process according to claim 1, wherein step (B), when the monoacylhydrazine having general formula (III) is isolated in its raw state by means of filtration, is carried out in the presence of a polar organic solvent, the reaction is carried out at reflux temperature and subsequently, upon cooling to 0° C., the symmetrical diacylhydrazine having general formula (I) and the alkyl-pyrazolone or aryl-pyrazolone having general formula (V), precipitate: the precipitate is filtered and dried in an oven at 50° C.–100° C., under vacuum, a hydrocarbon solvent immiscible with water is added to the above precipitate, and the separation of the symmetrical diacylhydrazine having general formula (I) from the alkyl-pyrazolone or aryl-pyrazolone having general formula (V), is effected by means of one or more hot aqueous washings, at a temperature ranging from 85° C. to 125° C., at a pressure ranging form 1 kg/cm² to 4 kg/cm².

35. The process of claim 34, wherein said polar organic solvent is butanol, propanol, amyl alcohol or dimethylformamide and said hydrocarbon solvent is toluene or xylene.

36. The process according to claim 1, wherein the esters having general formula (II) which can be used in step (A) are: methyl or ethyl acetate, methyl or ethyl butyrate, methyl or ethyl cyanoacetate, methyl or ethyl propionate, methyl or ethyl octanoate, methyl or ethyl benzoate, methyl or ethyl dodecanoate, methyl or ethyl salicylate, methyl 4-methyl-benzoate, ethyl isoamylacetate, ethyl phenylacetate, methyl 3-(3,5-di-t-butyl-4-hydroxyphenyl)-propionate.

37. The process according to claim 1, wherein the monoacylhydrazines having general formula (III) obtained in step (A) are: acetylhydrazine, cyanoacetylhydrazine, butyrylhydrazine, propionylhydrazine, n-octanoylhydrazine, isoamylacetylhydrazine, glycolylhydrazine, benzoylhydrazine, 4-methylbenzoylhydrazine, salicyloylhydrazine, dodecanoylhydrazine, phenylacetylhydrazine, 3-(3,5-di-t-butyl-4-hydroxyphenyl) propionylhydrazine.

38. A process for the preparation of symmetrical diacylhydrazines having general formula (I) comprising the reaction of a monocylhydrazine having general formula (III) with a β-ketoester having general formula (IV), operating as described for step (B) in claim 1.

39. The process according to claim 1, wherein the β-ketoesters having general formula (IV) which can be used in step (B) are: methyl acetoacetate, ethyl acetoacetate, t-butyl acetoacetate, ethyl benzoyl acetate.

40. The process according to claim 1, wherein the symmetrical diacylhydrazines having general formula (I) obtained are: 1,2-di-propionylhydrazine, 1,2-di-butyrylhydrazine, 1,2-di-isoamylacetylhydrazine, 1,2-di-glycolylhydrazine, 1,2-di-acetylhydrazine, 1,2-di-n-octanoylhydrazine, 1,2-di-benzoylhydrazine, 1,2-di-salicyloylhydrazine, 1,2-di-dodecanoylhydrazine, 1,2-diphenylacetylhydrazine, 1,2-di-p-toluoylhydrazine, N,N'-bis-[3-(3,5-di-t-butyl-4-hydroxyphenyl)propionyl] hydrazine.

41. The process of claim 1, wherein said hydrocarbon solvent is toluene, xylene, isooctane, cyclohexane, methylcyclohexane, nonane, decane, undecane or decaline.

* * * * *